United States Patent [19]
Tao

[11] Patent Number: 5,893,307
[45] Date of Patent: Apr. 13, 1999

[54] PLIERS WITH BIASING ELEMENT

[76] Inventor: Liang-Che Tao, 957 Ashton Pl., Carmel, Id. 46033

[21] Appl. No.: 08/845,615

[22] Filed: Apr. 25, 1997

[51] Int. Cl.$^6$ .................................................. B25B 7/02
[52] U.S. Cl. .................................................. 81/427; 30/261
[58] Field of Search .................... 81/300, 342, 427, 81/427.5; 30/261

[56] References Cited

U.S. PATENT DOCUMENTS

| | | |
|---|---|---|
| 258,920 | 6/1882 | Hayden . |
| 1,486,057 | 3/1924 | Switzer . |
| 2,827,815 | 3/1958 | Smoyak . |
| 5,522,289 | 6/1996 | Eggert . |
| 5,522,290 | 6/1996 | Visser et al. . |
| 5,607,344 | 3/1997 | Endres . |

Primary Examiner—James G. Smith
Attorney, Agent, or Firm—Locke Reynolds

[57] ABSTRACT

A pair of pliers including a first plier element having a first handle portion and a first jaw portion defining a plurality of first protections. A deflected beam biasing element including a distal end is integrally formed with the first plier element. A second plier element includes a second handle portion, a second jaw portion defining a plurality of second projections, a contact surface having a first end and a second end, and a stop disposed proximate to the first end. A pivot element is provided to pivotally secure the first prier element to the second plier element so that relative pivoting movement of the first handle portion towards the second handle portion causes the first jaw portion to move towards the second jaw portion, the first end is disposed closer to the pivot pin than is the second end, and the distal end slidingly engages the contact surface. Force exerted by the finger portion against contact surface biases towards a normally open position with the first handle portion urged towards separation from the second handle portion, the first jaw portion urged towards separation from the second jaw portion, and the distal end urged towards the first end and bearing against the stop. Pivoting of the first handle portion towards the second handle portion causes the finger portion to deflect away from the pivot pin as the distal end slides towards the second end against biasing force. The position of the projections relative to the distal tips of the jaw portions, and the gaps between proximate pairs of the projections on the jaw portions can be selected to facilitate surrounding and subsequent gripping of a hub portion of a needle employed in a hypodermic syringe needle assembly.

18 Claims, 2 Drawing Sheets

PLIERS WITH BIASING ELEMENT

BACKGROUND OF THE INVENTION

1. Field of the Invention

The present Invention generally relates to pliers, and more particularly to pliers that include an element for biasing the pliers in an open position.

2. Description of the Prior Art

Pliers having a biasing element for urging the pliers towards an open position are well known, and are useful for grasping articles of preselected sizes and for repeatedly grasping similar articles. Generally, such pliers include plier components and a separate biasing element. Moreover, available pliers including elements biasing towards an open position generally do not limit the extent to which the pliers may be opened.

Despite the availability of such devices, there exists a need in the art for an improved pliers with biasing element that are capable of being used by the efforts of a single hand to pick up, grip, move, and release an object of a preselected size, yet limits the extent to which the pliers may be opened, and, In addition, are formed of a minimum number of components that are durable, inexpensive, and easily cleaned and maintained. There particularly exists a need in the art for an improved pliers particularly adapted for use in removing needles from hypodermic syringes.

SUMMARY OF THE INVENTION

In order to aid in the understanding of the present invention, it can be stated in essentially summary form that it is directed to a pair of pliers including a first plier element having a flexible resilient finger portion, a second plier element having a contact surface including a first end and a second end, and a stop disposed proximate to the first end, and a pivot adapted to secure the first plier element to the second plier element so that the first end is disposed closer to the pivot than is the second end and the resilient finger portion slidingly engages the contact surface, for relative pivoting movement between a normally open position where the resilient finger portion is disposed proximate to the first end and bears against the stop to limit relative pivoting movement and a closed position where the resilient finger portion deflects away from the pivot and exerts biasing force against the contact surface for urging the pliers towards the open position.

More specifically, the present invention is directed to a pair of pliers including a first plier element having a first handle portion and a first jaw portion defining a plurality of first projections. A deflected beam biasing element, in the form of a flexible resilient finger portion including a distal end, is mounted to the first handle portion. The deflected beam biasing element can be integrally formed with the first plier element. A second plier element includes a second handle portion and a second jaw portion defining a plurality of second projections. The second plier element further defines a contact surface having a first end and a second end, and a stop disposed proximate to the first end. The second handle portion can be formed to define a finger aperture and a plurality of finger indentations.

A pivot element, such as a pivot pin, is provided to pivotally secure the first plier element to the second plier element so that relative pivoting movement of the first handle portion towards the second handle portion causes the first jaw portion to move towards the second jaw portion. With the first end disposed closer to the pivot pin than is the second end, the distal end of the resilient finger slidingly engages the contact surface, and the second projections are positioned for engagement proximate to the first projections.

Biasing force exerted by the finger portion against contact surface urges the present invention towards a normally open position with the first handle portion urged towards separation from the second handle portion, the first jaw portion urged towards separation from the second jaw portion, and the distal end of the resilient finger urged towards the first end and bearing against the stop. As a result, the pliers are normally disposed in an open position with the first handle portion separated from the second handle portion, but with separation of the first handle portion from the second handle portion limited by the distal end of the resilient finger bearing against the stop.

Force exerted for relative pivoting movement of the first handle portion towards the second handle portion to a closed position causes the finger portion to deflect away from the pivot pin as the distal end slides towards the second end against biasing force exerted by the finger portion. As the pliers move towards the closed position, the first jaw portion moves toward the second jaw portion, and the second projections move towards engagement with the first projections.

The pliers can be formed so that at least one of the first projections is disposed at a distal tip of the first jaw portion and at least one of the second projections is disposed at a distal tip of the second jaw portion, whereby the pliers may be used to pick up and grip small objects. Further, by forming the first and second plier elements so that gaps between proximate pairs of the first and second projections vary, the present invention may be used to grip and hold objects of varying sizes. In one preferred embodiment of the present invention, the position of the projections relative to the distal tips of the jaw portions, and the gaps between proximate pairs of the first and second projections are selected to facilitate surrounding and subsequent gripping of a hub portion of a needle employed in a hypodermic syringe needle assembly.

In use, the pliers, normally disposed in the open position, may be held in a hand with a finger disposed through the finger aperture and one or more fingers proximate to the finger indentations. In the open position, relative separation of the first and second jaw portions are limited by the distal end bearing against the stop. Separation of the first and second jaw portions can be chosen so that an object of a preselected size may conveniently fit between one of more of the first and second projections. After the first and second jaw portions are placed on opposing sides of an object to be gripped, the first and second it handle portions are pinched together against the biasing force of the finger portion, with the distal and sliding along the contact surface from the first end towards the second end, and with deflection of the finger portion increasing with movement towards the closed position, due to the first end being disposed closer to the pivot pin than is the second end. After the desired object is gripped between the first and second jaw portions, the object may be held using the efforts of one hand to maintain the present invention in the closed position, and moved to a desired location. The held object may then be released by reducing the hand's pinching force on the first and second handle portions, with the pliers returning to the open position due to the urging of the finger portion against the contact surface.

Further advantages of the present invention will be apparent from a study of the following portion of the specification, the claims, and the attached drawings.

DETAILED DESCRIPTION OF THE PREFERRED EMBODIMENTS

The following portion of the specification, taken in conjunction with the drawings, sets forth the preferred embodiments of the present invention. The embodiments of the invention disclosed herein are the best mode contemplated for carrying out the invention in a commercial environment, although it should be understood that various modifications can be accomplished within the parameters of the present invention.

Figure 1:
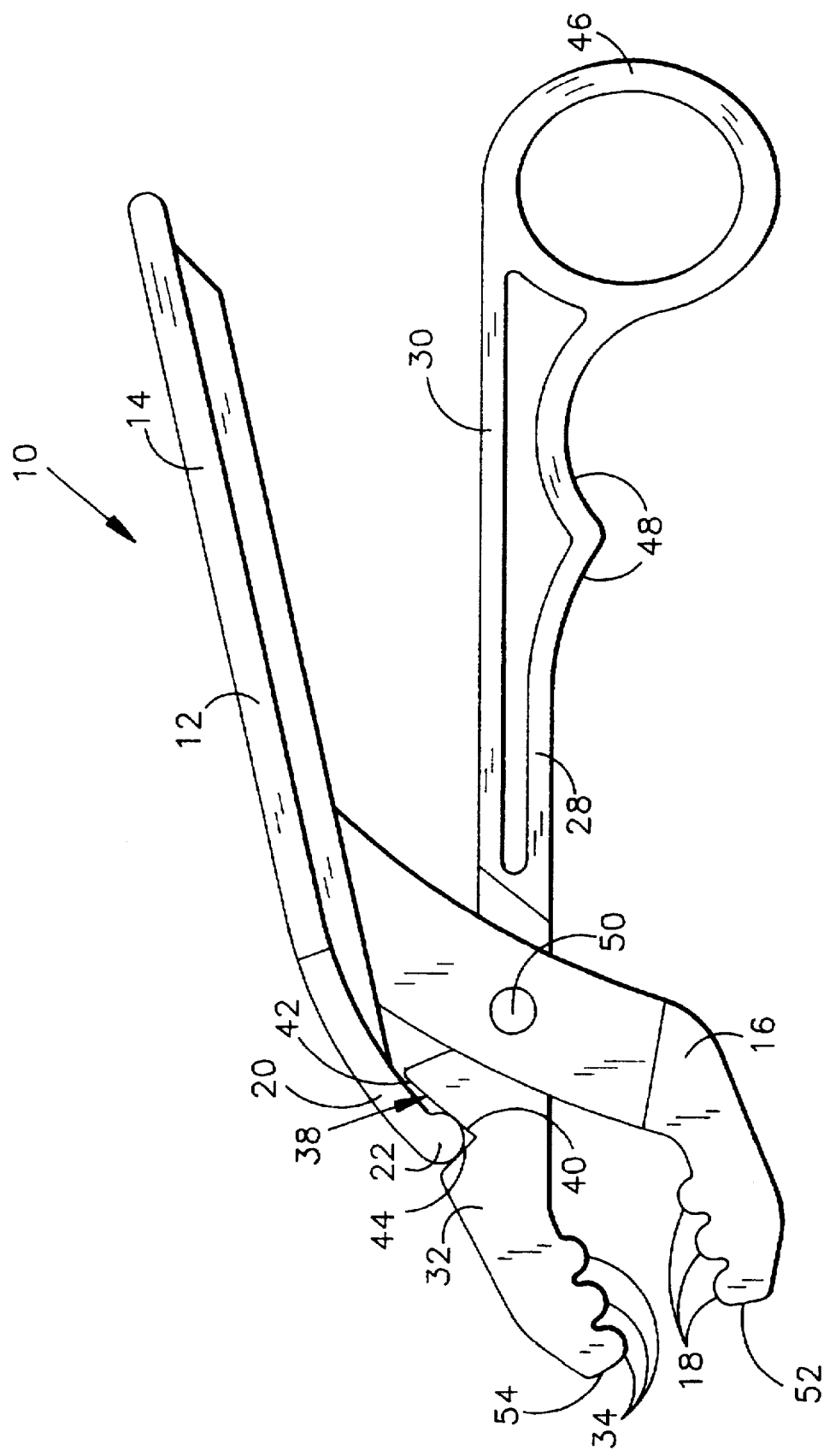
FIG. 1 is a side view of a pliers with biasing element representing the present invention, depicted in the open position.
Figure 2:
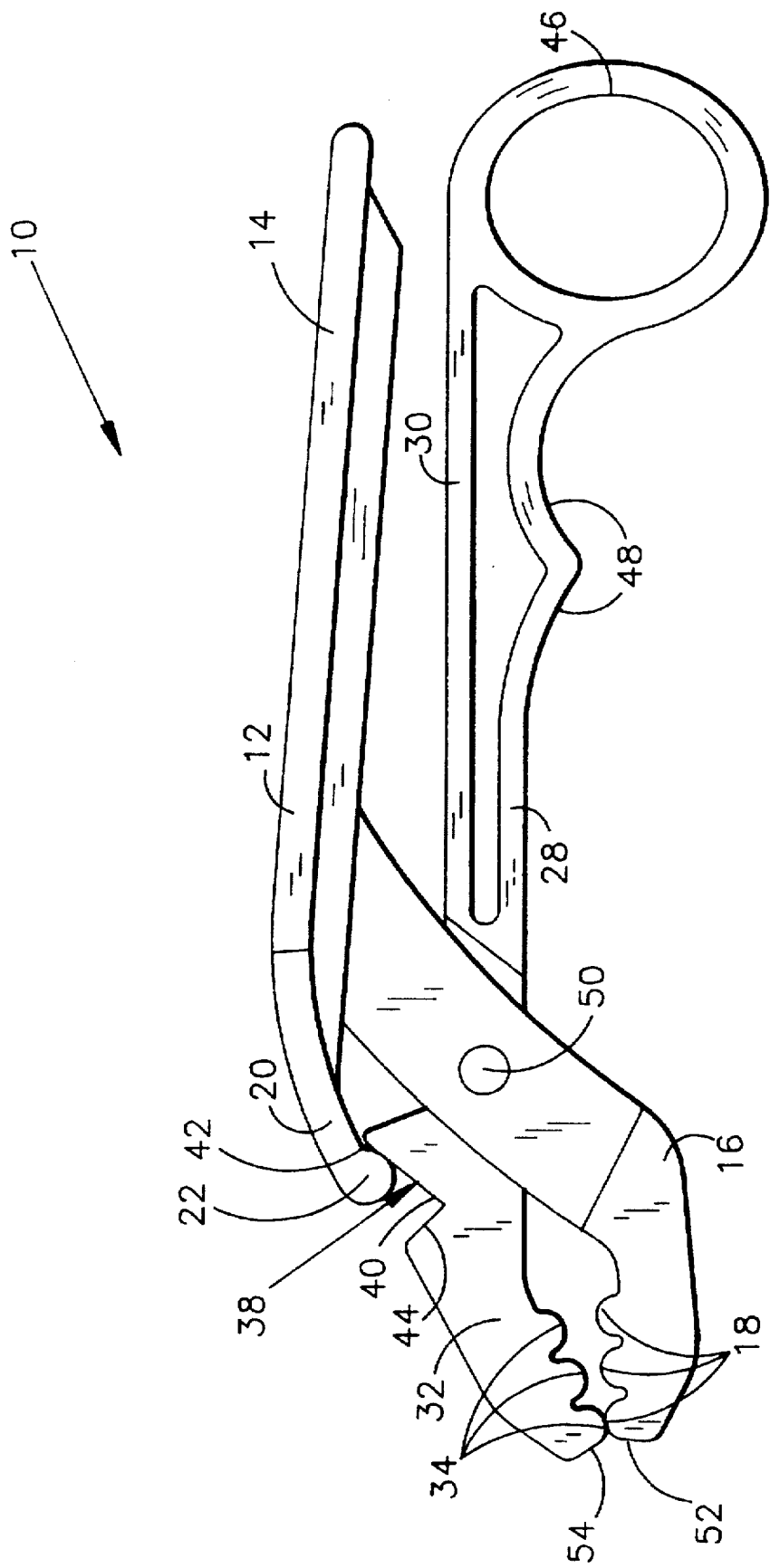
FIG. 2 is a side view of a pliers with biasing element representing the present invention, depicted in the closed position.

Referring now to the drawings for a detailed description of the present invention, reference is first made to FIGS. 1 and 2, generally depicting pair of pliers 10 including first plier element 12 having first handle portion 14 and first jaw portion 16 defining a plurality of first projections 18. A deflected beam biasing element, in the form of a flexible resilient finger portion 20 including distal end 22, is mounted to first handle portion 14. The deflected beam biasing element can be integrally formed with first plier element 12, and in a preferred embodiment, the deflected beam biasing element and first plier element 12 can be integrally formed of any of a number of suitable sturdy, flexible, and resilient materials such as plastics. Second plier element 28 includes second handle portion 30 and second jaw portion 32 defining a plurality of second projections 34. Second plier element 28 further defines contact surface 38 having first end 40 and second end 42, and stop 44 disposed proximate to first end 40. Second handle portion 30 can be formed to define finger aperture 46 and a plurality of finger indentations 48.

A pivot element, such as pivot pin 50, is provided to pivotally secure first plier element 12 to second plier element 28 so that relative pivoting movement of first handle portion 14 towards second handle portion 30 causes first jaw portion 16 to move towards second jaw portion 32. With first end 40 disposed closer to pivot pin 50 than is second end 42, distal end 22 slidingly engages contact surface 38, and second projections 34 are positioned for engagement proximate to first projections 18.

Biasing force exerted by finger portion 20 against contact surface 38 urges pliers 10 towards a normally open position as shown in FIG. 1, with first handle portion 14 urged towards separation from second handle portion 30, first jaw portion 16 urged towards separation from second jaw portion 32, and distal end 22 urged towards first end 40 and bearing against stop 44. In this way, pliers 10 are normally disposed in an open position with first handle portion 14 separated from second handle portion 30, but with separation of first handle portion 14 from second handle portion 30 limited by distal end 22 bearing against stop 44.

Force exerted for relative pivoting movement of first handle portion 14 towards second handle portion 30 to a closed position, as shown in FIG. 2, causes finger portion 20 to deflect away from pivot pin 50 as distal and 22 slides towards second and 42 against biasing force exerted by finger portion 20. As pliers 10 move towards the closed position, first jaw portion 16 moves toward second jaw portion 32, and second projections 34 move towards engagement with first projections 18.

As shown in FIGS. 1 and 2, pliers 10 can be formed so that at least one first projection 18 is disposed at a distal tip 52 of first jaw portion 16 and at least one second projection 34 is disposed at a (distal tip 54 of second jaw portion 32, the present invention maybe used to pick up and grip small objects. Further, by forming first and second plier elements 12 and 28 so that gaps between proximate pairs of first and second projections 18 and 34 vary, the present invention may be used to grip and hold objects of varying sizes.

In use, pliers 10, normally disposed in the open position illustrated in FIG. 1, may be held in a hand with a finger disposed through finger aperture 46 and one or more fingers proximate to finger indentations 48. In the open position, relative separation of first and second jaw portions 16 and 32 are limited by distal end 22 bearing against stop 44. For instance, separation of first and second jaw portions 16 and 32 may be chosen so that an object of a preselected size may conveniently fit between one of more of first and second projections 18 and 34. On one preferred use of the present invention, the position of the first and second projections 18 and 34 relative to the distal tips 52 and 54 of the jaw portions 16 and 32 are selected to facilitate surrounding and subsequent gripping of a hub portion of a needle employed in a hypodermic syringe needle assembly as the needle is lying on a flat surface such as a table top. Additionally, the separation of the projections 18 and 34 in the first and second jaw portions 16 and 32 facilitate the installation and removal of the needle assembly from the hypodermic syringe barrel while avoiding close proximity between the needle assembly and the hand operating the pliers.

After first and second jaw portions 16 and 32 are placed on opposing sides of an object to be gripped, first and second handle portions 14 and 30 are pinched together against the biasing force of finger portion 20, with distal end 22 sliding along contact surface 38 from first end 40 towards second end 42, and with deflection of finger portion 20 increasing with movement towards the closed position, due to first end 40 being disposed closer to pivot pin 50 than is second end 42. After the desired object is gripped between first and second jaw portions 16 and 32, the object may be held using the efforts of one hand to maintain the present invention in the closed position, and moved to a desired location. The held object may then be released by reducing the hand's pinching force on first and second handle portions 14 and 30, with pliers 10 returning to the open position due to the urging of finger portion 20 against contact surface 38.

As noted, the deflected beam biasing element and first plier element 12 can be integrally formed of a sturdy, flexible, and resilient plastic material. In addition, by forming second plier element 28 and pivot pin 50 of a similar material, the present invention can be easily and inexpensively constructed, yet be easily cleaned and durable.

The present invention having been described in its preferred embodiments, it is clear that the present invention is susceptible to numerous modifications and embodiments within the ability of those skilled in the art and without the exercise of the inventive faculty. Accordingly, the scope of the present invention is defined as set forth by the scope of the following claims.

What is claimed is:

1. A pair of pliers comprising:

a first plier element having a flexible resilient finger portion;

a second plier element having a contact surface including a first end and a second end, and a stop disposed proximate to the first end; and a pivot adapted to secure the first plier element to the second plier element so that the first end is disposed closer to the pivot than is the second end and the finger portion slidingly engages the contact surface, for relative pivoting movement between a normally open position where the finger portion is disposed proximate to the first end and bears against the stop to limit relative pivoting movement and a closed position where the finger portion deflects away from the pivot and exerts biasing force against the contact surface for urging towards the open position.

2. A pair of pliers as recited in claim 1, wherein the finger portion is adapted to slide away from contact with the stop and towards the second end against biasing force exerted by the finger portion during pivoting movement from the open position to the closed position.

3. A pair of pliers as recited in claim 1, wherein the first plier element is formed of plastic.

4. A pair of pliers as recited in claim 1, wherein the finger portion includes a distal end, and the pivot is adapted to secure the first plier element to the second plier element so that the distal end slidingly engages the contact surface and is disposed proximate to the first end and bears against the stop to limit relative pivoting movement when the first and second plier elements are disposed in the open position.

5. A pair of pliers as recited in claim 4, wherein the distal end is adapted to slide towards the second end against biasing force exerted by the finger portion during pivoting movement from the open position to the closed position.

6. A pair of pliers as recited in claim 1, wherein the first plier element includes a first jaw portion having a plurality of first projections and the second plier element includes a second jaw portion having a plurality of second projections adapted for engagement with the plurality of first projections.

7. A pair of pliers as recited in claim 6, wherein at least one first projection is disposed at a distal tip of the first jaw portion and at least one second projection is disposed at a distal tip of the second jaw portion.

8. A pair of pliers as recited in claim 6, wherein the first jaw portion and the second jaw portion are adapted to grip an object of a preselected size when the first and second plier elements are disposed in the closed position.

9. A pair of pliers as recited in claim 8, wherein the first jaw portion and the second jaw portion are adapted to grip a hub portion of a syringe needle assembly when the first and second plier elements are disposed in the closed position.

10. A pair of pliers comprising:

a first plier element having a first jaw portion including a plurality of first projections and a flexible resilient finger portion including a distal end;

a second plier element having a second jaw portion including a plurality of second projections, a contact surface including a first end and a second end, and a stop disposed proximate to the first end; and a pivot adapted to secure the first plier element to the second plier element so that the first end is disposed closer to the pivot than is the second end, the distal end slidingly engages the contact surface, and the second projections are aligned for engagement with the first projections, for relative pivoting movement between a normally open position where the distal end is disposed proximate to the first end and bears against the stop to limit relative pivoting movement, and a closed position where the finger portion deflects away from the pivot and exerts biasing force against the contact surface for urging towards the open position, the distal end adapted to slide away from contact with the stop and towards the second end against biasing force exerted by the finger portion during pivoting movement from the open position to the closed position.

11. A pair of pliers as recited in claim 10, wherein at least one first projection is disposed at a distal tip of the first jaw portion and at least one second projection is disposed at a distal tip of the second jaw portion, and the first jaw portion and the second jaw portion are adapted to grip a hub portion of a syringe needle assembly when the first and second plier elements are disposed in the closed position.

12. A pair of pliers comprising:

a first plier element having a first handle portion and a first jaw portion;

a deflected beam biasing element mounted to the first handle portion and including a distal end;

a second plier element having a second handle portion, a second jaw portion, a contact surface having a first end and a second end, and a stop disposed proximate to the first end; and a pivot element adapted to pivotally secure the first plier element to the second plier element so that relative movement of the first handle portion towards the second handle portion causes the first jaw portion to move towards the second jaw portion, the first end is disposed closer to the pivot element than is the second end, the distal end slidingly engages the contact surface, and biasing force exerted by the biasing element against the contact surface urges the first handle portion towards separation from the second handle portion, the first jaw portion towards separation from the second jaw portion, and the distal end towards the first end and bearing against the stop to limit separation of the first handle portion from the second handle portion, whereby force exerted to move the first handle portion towards the second handle portion causes the biasing element to deflect away from the pivot element as the distal end slides towards the second end against biasing force exerted by the biasing element portion.

13. A pair of pliers as recited in claim 12, wherein the deflected beam biasing element is integrally formed with the first plier element.

14. A pair of pliers as recited in claim 13, wherein the deflected beam biasing element and the first plier element are formed of plastic.

15. A pair of pliers as recited in claim 13, wherein the first jaw portion includes a plurality of first projections and the second jaw portion includes a plurality of second projections adapted for engagement with the plurality of first projections.

16. A pair of pliers as recited in claim 15, wherein at least one first projection is disposed at a distal tip of the first jaw portion and at least one second projection is disposed at a distal tip of the second jaw portion.

17. A pair of pliers as recited in claim 16, wherein the first jaw portion and the second jaw portion are adapted to grip an object of a preselected size when the first and second plier elements are disposed in the closed position.

18. A pair of pliers as recited in claim 17, wherein the first jaw portion and the second jaw portion are adapted to grip a hub portion of a syringe needle assembly when the first and second plier elements are disposed in the closed position.

* * * * *